United States Patent
Mitusina

(10) Patent No.: US 8,052,706 B2
(45) Date of Patent: *Nov. 8, 2011

(54) FLEXIBLE INNER MEMBER HAVING A FLEXIBLE REGION COMPRISING A LABYRINTHINE CUT

(75) Inventor: Miroslav Mitusina, Ruskin, FL (US)

(73) Assignee: B&M Precision, Inc., Ruskin, FL (US)

( * ) Notice: Subject to any disclaimer, the term of this patent is extended or adjusted under 35 U.S.C. 154(b) by 418 days.

This patent is subject to a terminal disclaimer.

(21) Appl. No.: 12/170,906

(22) Filed: Jul. 10, 2008

(65) Prior Publication Data

US 2010/0010526 A1  Jan. 14, 2010

(51) Int. Cl.
*A61B 17/14* (2006.01)

(52) U.S. Cl. ............................. 606/180; 606/79; 606/170

(58) Field of Classification Search .................. 606/167, 606/170, 180, 79; 623/1.15
See application file for complete search history.

(56) References Cited

U.S. PATENT DOCUMENTS

| | | | |
|---|---|---|---|
| 4,646,738 A | 3/1987 | Trott | |
| 5,152,744 A | 10/1992 | Krause et al. | |
| 5,286,253 A | 2/1994 | Fucci | |
| 5,322,505 A | 6/1994 | Krause et al. | |
| 5,437,630 A | 8/1995 | Daniel et al. | |
| 5,510,070 A | 4/1996 | Krause et al. | |
| 5,529,580 A | 6/1996 | Kusunoki et al. | |
| 5,540,708 A | 7/1996 | Lim et al. | |
| 5,620,415 A | 4/1997 | Lucey et al. | |
| 5,620,447 A | 4/1997 | Smith et al. | |
| 6,053,922 A | 4/2000 | Krause et al. | |
| 6,533,749 B1 | 3/2003 | Mitusina et al. | |
| 6,656,195 B2 * | 12/2003 | Peters et al. | 606/159 |
| 7,276,074 B2 | 10/2007 | Adams et al. | |
| 7,338,495 B2 | 3/2008 | Adams | |
| 7,727,272 B2 * | 6/2010 | Schlun et al. | 623/1.15 |
| 2005/0090849 A1 | 4/2005 | Adams | |

FOREIGN PATENT DOCUMENTS

DE 3828478 A1 5/1989

* cited by examiner

*Primary Examiner* — Elizabeth Houston
*Assistant Examiner* — Sarah Webb

(57) ABSTRACT

A flexible inner member for rotation within an angled outer tubular member of a rotary tissue cutting instrument to cut anatomical tissue includes a flexible region for conforming to the configuration of an angled region of the outer tubular member and formed of a labyrinthine cut through a cylindrical wall of a tubular body of the inner member. The labyrinthine cut includes a plurality of labyrinthine areas rotationally spaced on the tubular body and in which the labyrinthine cut defines a labyrinth configuration including minor curves of opposed curvature respectively arranged within major curves of opposed curvature, with each of the minor curves being continuous with a major curve of opposed curvature thereto.

20 Claims, 3 Drawing Sheets ved within the angled outer tubular member. A cutting element at a distal end of the inner member is exposed from an opening at a distal end of the outer member to cut anatomical tissue at the surgical site when the inner member is rotated within the outer member. The inner member is ordinarily rotated within the outer member via a powered surgical handpiece coupled to proximal ends of the outer and inner members, with the handpiece being maintained externally of the patient's body. The outer tubular member has one or more angled, curved or bent regions along its length to provide an angled configuration that facilitates positioning of the cutting element at the surgical site when the instrument is introduced in the patient's body, and particularly when the instrument is introduced through a narrow or small size, natural or artificially created entry opening in the patient's body. The inner tubular member is provided with one or more flexible regions to reside within the one or more angled, curved or bent regions of the outer member for transmitting torque to rotate the cutting element while conforming to the angled configuration of the outer member. The angled configuration of the outer member is particularly beneficial in facilitating positioning of the cutting element at the surgical site where there is a non-straight path in the body from the entry opening to the surgical site. In such cases, angled rotary tissue cutting instruments are usually better suited to access the surgical site more easily and quickly, and with less trauma to the patient, than are rotary tissue cutting instruments in which the outer tubular member is longitudinally straight. In many surgical procedures performed using rotary tissue cutting instruments, the internal lumen of the inner tubular member is used to transmit suction to the surgical site to aspirate anatomical tissue and/or fluid through the inner member. In addition, an annular gap or clearance between the internal diameter of the outer member and the external diameter of the inner member is commonly used as an irrigation passage to supply irrigation fluid to the surgical site.

One design advantage in rotary tissue cutting instruments is to minimize the external diametric size of the outer member to allow introduction of the instrument in the patient's body through entry openings as small as possible in size and/or to facilitate advancement of the instrument to the surgical site with as little trauma as possible to the patient. Another design advantage in rotary tissue cutting instruments is to maximize the internal diameter of the inner tubular member so that aspiration of tissue and/or fluid through the inner member can be accomplished with greater efficiency and with less risk of clogging. Yet a further design advantage in rotary tissue cutting instruments is to maintain an appropriate annular clearance between the internal diameter of the outer tubular member and the external diameter of the inner member to avoid jamming of the instrument and/or to provide efficient flow of irrigation fluid between the outer and inner members. In angled rotary tissue cutting instruments, it would also be a design advantage to minimize the number of structural components or parts required for the flexible region of the inner member, thereby reducing manufacturing and material costs, as well as reducing the risk of operational problems arising from structural complexity and/or multiple structural components. The foregoing design advantages must necessarily be balanced against the need to maintain sufficient strength and rigidity in the flexible inner members of angled rotary tissue cutting instruments when transmitting torque via the flexible regions, particularly considering that angled rotary tissue cutting instruments must oftentimes be designed to operate at high rotational speeds and to withstand the forces imposed when cutting very hard or tenacious anatomical tissue.

Various designs previously proposed for the flexible regions in the inner members of angled rotary tissue cutting instruments have limited the extent to which the aforementioned design advantages can be optimized in angled rotary tissue cutting instruments. Some of the deficiencies associated with prior designs proposed for the flexible regions in the inner members of angled rotary tissue cutting instruments include increased radial thickness of the annular wall of the inner tubular member along the flexible region resulting in a larger external diameter and/or smaller internal diameter for the inner member, structural complexity and/or the need for multiple assembled structural parts to form the flexible region, constriction of the internal diameter of the flexible region when transmitting torque within an angled region of the outer tubular member, longitudinal stretching of the flexible region, and insufficient strength and rigidity in the flexible region limiting the range of bend angles over which the flexible region is able to effectively transmit torque. Designs for the flexible regions of inner tubular members of angled rotary tissue cutting instruments that result in the inner tubular member being of larger external diametric size normally require that the angled outer tubular member be of larger external diametric size in order to rotatably receive the inner member while maintaining the appropriate annular clearance between the outer and inner members. Designs for the flexible regions of inner tubular members of angled rotary tissue cutting instruments that result in the inner tubular member having a smaller internal diameter or that result in constriction of the internal diameter will typically have a negative impact on the ability to aspirate tissue and/or fluid through the inner tubular member. Designs for the flexible regions of inner tubular members of angled rotary tissue cutting instruments that involve structural complexity and/or multiple assembled structural parts generally result in the inner tubular member being of higher cost and at increased risk of operational problems. Operational problems are also more likely to occur in inner tubular members of angled rotary tissue cutting instruments in which the design for the flexible region in the inner member makes the flexible region prone to longitudinal stretching.

In some flexible inner tubular members of angled rotary tissue cutting instruments, the flexible regions are formed of a plurality of concentric spirals, typically an inner spiral, a middle spiral and an outer spiral attached to one another at their ends. Each spiral is formed by winding a flat strip of material, with alternating spirals being wound in opposite rotational directions about a central longitudinal axis of the inner member as represented by U.S. Pat. No. 4,646,738 to Trott, U.S. Pat. No. 5,286,253 to Fucci and U.S. Pat. No. 5,540,708 to Lim et al. It has also been proposed to provide shafts having flexible regions made up of concentric coils of wound wire of circular cross-section, rather than wound flat strips of material, as represented by U.S. Pat. No. 5,437,630 to Daniel et al and U.S. Pat. No. 5,529,580 to Kusunoki et al and by German Patent DE 3828478 A1. The radial dimension or thickness of the annular wall of a flexible region comprised of multiple concentric spirals or coils tends to be substantial since it includes the individual thickness of each spiral or coil. Flexible regions of this type tend to result in flexible inner tubular members of larger external diametric sizes requiring diametrically larger outer tubular members, and/or of smaller internal diameters leading to reduced aspiration capability. In addition, flexible inner tubular members having these types of flexible regions will ordinarily be associated with higher material costs due to the multiple structural components involved and with higher manufacturing costs associated with producing and assembling the different structural components. The risk of operational problems may be greater due to the presence of multiple structural components and increased structural complexity, and the securement or attachment sites for the multiple spirals or coils present the potential for structural failure.

Another design approach for the flexible regions in the flexible inner tubular members of angled rotary tissue cutting instruments involves a single continuous spiral or helical cut formed in an inner tube, and one or more layers of spiral wrap disposed over the cut region of the inner tube as represented by U.S. Pat. No. 6,533,749 B1 to Mitusina et al and U.S. Pat. No. 6,656,195 B2 to Peters et al, and by U.S. Patent Application Publication No. US2005/0090849 A1 to Adams. The one or more layers of spiral wrap are each formed by winding a flat strip of material over the cut region in the inner tube and attaching the ends of the strip to the tube. The helical cut and the one or more layers of spiral wrap are arranged so that their rotational direction or turn about a central longitudinal axis of the inner member alternate in opposite directions. The Peters et al patent discloses the helical cut in the inner tube as having a dovetail pattern. The extent to which it is possible to minimize the radial dimension or thickness of the annular wall of a flexible region comprised of an inner tube and one or more layers of spiral wrap over a cut region of the tube is limited by the fact that the wall thickness of the inner tube and the thickness of each layer of spiral wrap contribute cumulatively to the radial dimension of the annular wall formed by the flexible region. Furthermore, the inner tube and each spiral wrap are separate structural components assembled during manufacture, giving rise to issues of increased cost and structural complexity.

U.S. Pat. No. 7,338,495 B2 to Adams is an example of a flexible region in a flexible inner tubular member of an angled rotary surgical cutting instrument formed of a helical cut in an inner tube, a layer of adhesive disposed over the cut region of the inner tube, and a heat shrunk sleeve disposed over the cut region of the inner tube and being bonded thereto by the adhesive. The helical cut is formed in the inner tube in a stepped pattern. Again, the radial thickness of the annular wall formed by the flexible region is made up of the individual thicknesses of the inner tube wall, the adhesive layer, and the wall of the sleeve. The flexible region requires multiple parts or materials in addition to the inner tube, and is still somewhat complicated from a manufacturing standpoint.

Flexible regions have also been provided in the inner tubular members of angled rotary tissue cutting instruments by forming disconnected slots or openings in an inner tube as illustrated by U.S. Pat. No. 5,152,744, U.S. Pat. No. 5,322,505 and U.S. Pat. No. 5,510,070 to Krause et al, U.S. Pat. No. 5,620,415 to Lucey et al, and U.S. Pat. No. 5,620,447 to Smith et al. Each slot is filled with a pliable material in a multi-step process carried out after the slots are formed. The preferred slot configuration described in the Krause et al, Lucey et al and Smith et al patents involves circumferentially discontinuous slots disposed in parallel spaced relation, the slots being arranged perpendicular to the longitudinal axis of the inner tube.

U.S. Pat. No. 6,053,922 to Krause et al pertains to a flexible shaft for reaming the medullary space in bones. In contrast to the flexible inner members of angled rotary tissue cutting instruments, the flexible shaft of Krause et al '922 is not designed to be rotatably disposed within a rigid outer tubular member, and is thusly not subject to the same design considerations as the inner members of rotary tissue cutting instruments and of angled rotary tissue cutting instruments in particular. In further distinction to the flexible inner tubular members of angled rotary tissue cutting instruments, the flexible shaft of Krause et al '922 is said to be an elongated tubular member of substantial wall thickness. A flexible inner tubular member of substantial wall thickness would be undesirable in an angled rotary tissue cutting instrument because it would result in a reduction in the internal diameter of the inner member, which would reduce aspiration capability, and/or it would require an outer member of larger external diameter to accommodate the inner member, which would require larger size entry openings in the patient's body for introduction of the instrument. The tubular member of Krause et al '922 comprises a slot, said to be of substantial width, extending spirally around the tubular member but in an undulating or serpentine pattern that forms complementary, mating interlocking shaped members in the tubular member that Krause et al '922 relies on to transmit torque.

Despite the numerous different design approaches previously proposed for the flexible inner members of angled rotary tissue cutting instruments, it was not recognized until the present invention that a flexible region comprising a labyrinthine cut formed in a tubular body of the inner member would provide numerous design advantages, including the advantages of design simplicity, eliminating the need for the flexible region to include an additional structure or layer of material over the cut region of the tubular body or within the cuts themselves, appropriate rigidity and torsional strength, resistance to stretching in the longitudinal axial direction of the inner member, preservation of the integrity of the internal diameter of the inner member, and the capability to transmit torque within angled outer tubular members having a broad range of bend angles.

SUMMARY OF THE INVENTION

The present invention is generally characterized in a flexible inner member for being rotatably disposed within an angled outer tubular member of a rotary tissue cutting instrument. The outer tubular member includes a distal end, a longitudinal internal passage, an open proximal end communicating with the passage, an angled region between the distal and proximal ends, and an opening in the distal end communicating with the internal passage. The flexible inner member has a distal end, a proximal end, a tubular body between the distal and proximal ends of the inner member, a cutting element at the distal end of the inner member, and a flexible region for being disposed within the angled region of the outer tubular member. When the inner member is rotatably disposed within the internal passage of the outer tubular member, the cutting element is exposed from the opening in the outer tubular member, and the flexible region is disposed within the angled region to transmit torque to rotate the cutting element while conforming to the configuration of the angled region. The tubular body of the inner member has a central longitudinal axis and a cylindrical wall having a wall thickness between external and internal diameter surfaces of the cylindrical wall. The flexible region comprises a labyrinthine cut in the tubular body extending entirely through the wall thickness of the cylindrical wall. The labyrinthine cut has a starting end on the tubular body and has a terminating end on the tubular body. The labyrinthine cut extends longitudinally along the tubular body and extends rotationally about the central longitudinal axis in a forward direction of the labyrinthine cut. The labyrinthine cut includes a plurality of labyrinthine areas rotationally spaced about the central longitudinal axis and in which the cut defines a labyrinth configuration. The labyrinth configuration defined by the cut in each labyrinthine area comprises a first major curve, a first minor curve joined to the first major curve and being of reverse curvature to the first major curve, a second minor curve of reverse curvature to the first minor curve, and a second major curve joined to the second minor curve and being of reverse curvature to the second minor curve. The first minor curve is disposed within the second major curve in spaced relation therewith, and the second minor curve is disposed within the first major curve in spaced relation therewith. The first minor curve is spaced from the second major curve in a direction radial to the second major curve. The second minor curve is spaced from the first major curve in a direction radial to the first major curve. The major curves have a radius of curvature, and the minor curves have a radius of curvature smaller than the radius of curvature of the major curves.

The labyrinthine cut comprises a plurality of cut sections in the tubular body arranged in succession from the starting end to the terminating end. Each labyrinth configuration is formed by the cooperative arrangement of a curled segment of a cut section with an opposed curled segment of a next succeeding cut section in the forward direction of the labyrinthine cut. One curled segment defines the first major curve and the first minor curve of the labyrinth configuration. The other curled segment defines the second major curve and the second minor curve of the labyrinth configuration. The cut sections have connecting segments that extend between successive labyrinth configurations. The connecting segments extend rotationally about the tubular body in the same rotational direction about the central longitudinal axis in the forward direction of the labyrinthine cut and at a non-perpendicular angle to the central longitudinal axis. The labyrinthine cut is a discontinuous cut, with each cut section being separated from the next succeeding cut section by a gap or break in the labyrinthine cut within the labyrinth configuration formed by the curled segments of the cut sections. The gap is situated between end points of the first and second minor curves of the curled segments that form the labyrinth configuration.

DETAILED DESCRIPTION OF THE INVENTION

Figure 1:
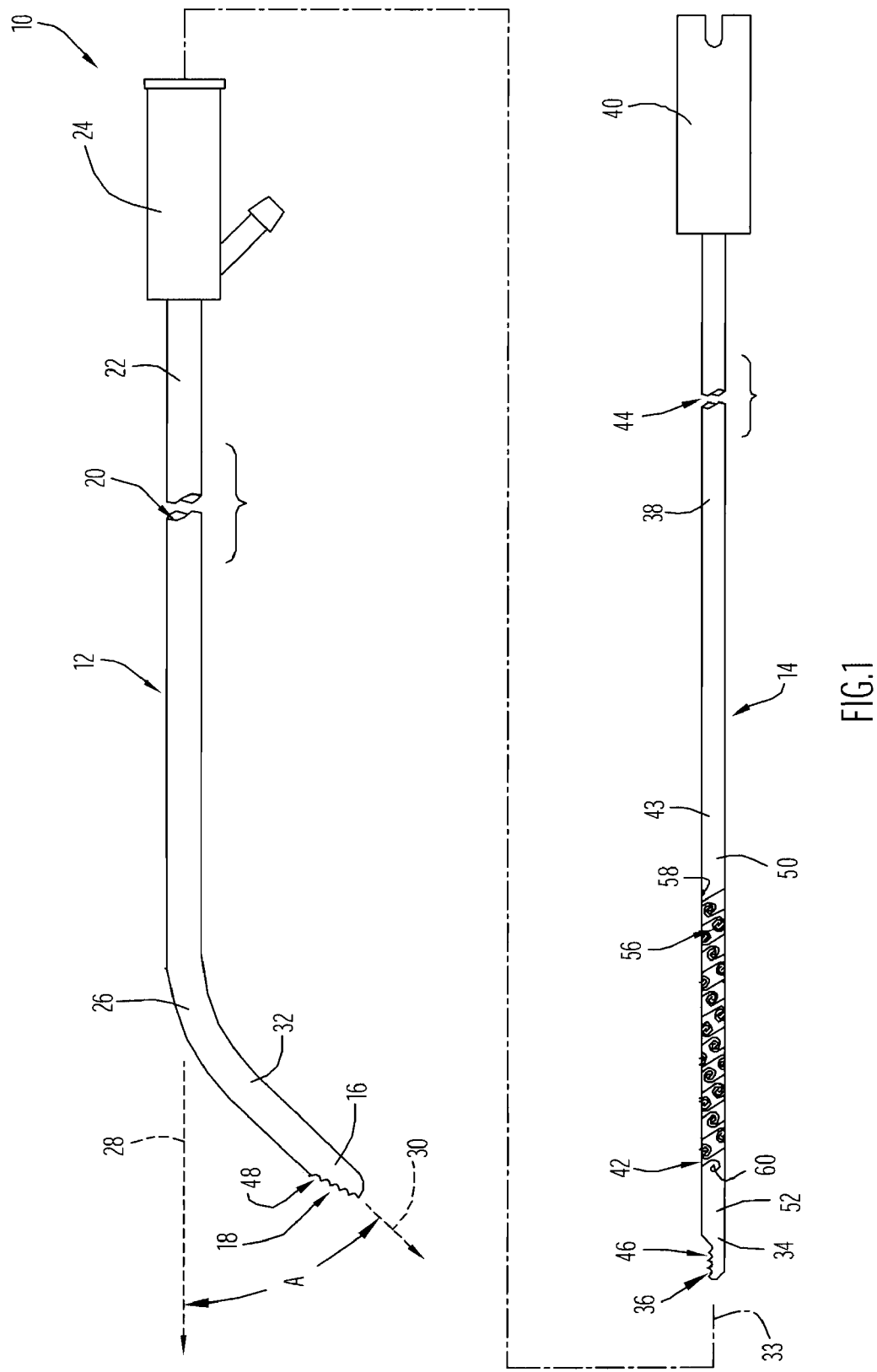
FIG. 1 is an exploded side view of an angled rotary tissue cutting instrument.

An angled rotary tissue cutting instrument 10 is depicted in FIG. 1 and comprises an elongate angled outer tubular member 12 and an elongate flexible inner member 14 for being rotatably disposed within the outer tubular member 12. The outer tubular member 12 has a distal end 16 with an opening 18 therein in communication with the internal passage 20 in the outer tubular member. The outer tubular member 12 has a proximal length portion 22 terminating at an open proximal end typically secured in an outer member hub 24 designed for engagement with a powered surgical handpiece (not shown) in a conventional manner. The outer tubular member 12 is provided with one or more angled, curved or bent regions 26 along the length thereof, such that the outer tubular member 12 has an angled configuration. Each angled region 26 in the outer tubular member 12 defines a bend angle A corresponding to the angle defined between length portions of the outer tubular member 12 that are joined by the angled region. The outer tubular member 12, for example, has a bend angle A defined between the central longitudinal axis 28 of the proximal length portion 22 of the outer member 12 and a central longitudinal axis 30 of a distal length portion 32 of the outer member 12 which is joined to the proximal length portion 22 by the angled region 26. The size and the direction of the bend angle A can vary individually for each angled region 26. The outer tubular member 12 illustrated in FIG. 1 has one angled region 26 with a bend angle A extending in a downward direction from proximal length portion 22.

As a result of its angled configuration, the outer tubular member 12 is not longitudinally straight along its length. However, the outer tubular member 12 can initially be provided in a longitudinally straight configuration, without the one or more angled regions 26, and can be bent from the longitudinally straight configuration in any suitable manner to obtain the angled configuration desired for the outer tubular member. Accordingly, bending the outer tubular member 12 from the longitudinally straight configuration to the desired angled configuration will involve bending the outer tubular member 12 as needed to obtain the desired number of angled regions 26 at the desired location or locations along the length of the outer tubular member and extending in the desired direction or directions at the desired bend angle or angles A. It should be appreciated that the outer tubular member 12 can be bent from the longitudinally straight configuration to the angled configuration with or without the flexible inner member 14 disposed within the outer tubular member 12. The outer tubular member 12 is rigid in a longitudinally straight configuration but is able to be bent to form the desired angled region(s) when sufficient bending force is applied. The outer tubular member 12 is or remains rigid after bending to form the one or more angled regions.

The inner member 14 has a central longitudinal axis 33, a distal end 34 provided with or formed as a cutting element 36, a proximal length portion 38 terminating at a proximal end that is typically secured in an inner member hub 40, and one or more flexible regions 42 between the cutting element 36 and the inner member hub 40. The one or more flexible regions 42 impart flexibility to the inner member that allows the inner member to bend along its central longitudinal axis 33. When the inner member 14 is assembled with the outer tubular member 12 to cut anatomical tissue, the inner member 14 will extend through the outer member hub 24 and will be rotatably disposed within the internal passage 20 of the outer tubular member 12 with the cutting element 36 exposed from the opening 18 in the outer member, with the one or more flexible regions 42 disposed within the one or more angled regions 26 of the outer member, and with the inner member hub 40 disposed proximally of the outer member hub 24 for engagement with the powered surgical handpiece. The powered surgical handpiece is operated in a conventional manner to rotate the inner member 14 relative to and within the outer tubular member 12, and the one or more flexible regions 42 transmit torque to rotate the cutting element 36 while conforming to the angled configuration of the outer tubular member 12. As the inner member 14 is rotated within the outer tubular member 12, the cutting element 36 exposed from the opening 18 will cut anatomical tissue contacted with the cutting element 36.

The inner member 14 comprises a cylindrical tubular body 43 coaxial with the central longitudinal axis 33 and having an internal lumen 44 extending longitudinally within the tubular body. The tubular body 43 preferably has an open end forming the proximal end of the inner member 14 and preferably extends from the proximal end of the inner member 14 to the cutting element 36, which is the case for tubular body 43. Preferably, the tubular body 43 is an integral and unitary or monolithic tube from the proximal end of the inner member 14 to the cutting element 36, which is also the case for tubular body 43. Accordingly, the flexible inner member 14 is a flexible inner tubular member. As described further below, the one or more flexible regions 42 are each formed by a labyrinthine cut in the tubular body 43.

The cutting element 36 can have various cutting configurations effective to cut anatomical tissue including the various cutting configurations conventionally used for the inner members of rotary tissue cutting instruments. The cutting element 36 can be a structure that is hollow or provided with an interior cavity or channel in communication with the lumen 44 of the tubular body 43. The cutting element 36 can be a structure formed separate from and attached to the tubular body 43. The distal end 34 of the inner tubular member 14 can have an opening 46 therein in communication with the internal lumen 44 of the inner member 14, and the opening 46 can communicate with the lumen 44 via the interior cavity or channel in the structure that forms the cutting element 36. The cutting configuration for the cutting element 36 can include one or more cutting surfaces or edges along the periphery of the opening 46 as is the case for the cutting element 36 of the inner member 14 depicted in FIG. 1. The cutting surfaces or edges of the cutting element 36 can be defined by cutting tooth formations, as is also the case for the cutting element 36 of inner member 14. The cutting surfaces or edges of the cutting element 36 can be defined by flute formations as in a bur tip, for example.

The distal end 16 of the outer tubular member 12 can be provided with or formed as a cutting element 48 that cooperates with the cutting element 36 of the inner member 14 to cut anatomical tissue. The cutting element 48 can have various cutting configurations effective to cut anatomical tissue in cooperation with the cutting element 36, and the various cutting configurations conventionally used for the outer members in rotary tissue cutting instruments can be used for the cutting configuration of the cutting element 48. The cutting configuration for the cutting element 48 can include one or more cutting surfaces or edges along the periphery of the opening 18 as is the case for the cutting element 48 of the outer tubular member 12 depicted in FIG. 1. The cutting surfaces or edges of the cutting element 48 can be defined by cutting tooth formations, as is also the case for the cutting element 48. Typically, the cutting elements 36 and 48 cooperate to cut anatomical tissue as a result of rotation of the one or more cutting surfaces or edges of the cutting element 36 past the one or more cutting surfaces or edges of the cutting element 48.

As the cutting element 36 is rotated, the opening 46 in the inner member 14 will come into alignment with the opening 18 in the outer tubular member 12, allowing anatomical tissue and/or fluid to enter the lumen 44 of the inner member 14 through the aligned openings 18 and 46. Through the application of vacuum or suction to the lumen 44, typically via a connection at a proximal end of the instrument 10 in a conventional manner, the lumen 44 can serve as an aspiration passage by which suction is applied at the surgical site via the aligned openings 18 and 46 and by which fluid and/or anatomical tissue is/are drawn into the lumen 44 through the aligned openings 18 and 46 for evacuation through the instrument 10.

In order for the inner member 14 to rotate within the outer tubular member 12 without jamming, an appropriate annular clearance or gap is present between the internal diameter of the outer tubular member 12 and the external diameter of the inner member 14 when the members 12 and 14 are assembled to cut tissue. The annular clearance or gap between the outer and inner members 12 and 14 can serve as an irrigation passage by which irrigation fluid supplied to the annular clearance, typically from a proximal end of the instrument 10, is conveyed distally and released at the surgical site through the opening 18 in the outer tubular member 12.

The inner member 14 can have a single flexible region 42 of sufficient length and at the appropriate location to reside in and conform to the configuration of one or more angled regions 26 in the outer tubular member 12. The inner member 14 can have a plurality of flexible regions 42, each of sufficient length and at the appropriate location to reside in and conform to the configuration of a corresponding angled region 26 in the outer tubular member 12. Each flexible region 42 can be disposed adjacent and/or between rigid or non-flexible length segments of the tubular body 43. The inner member 14 is an example of one having a single flexible region 42 disposed between rigid or non-flexible length segments 50 and 52 of the tubular body 43, the single flexible region 42 being located appropriately along the length of the inner member 14 to reside within the single angled region 26 in the outer tubular member 12 and being of sufficient length to conform to the configuration of the single angled region 26 when the inner member 14 is assembled with the outer member 12 to cut anatomical tissue. The length segment 50 of the tubular body 43 is part of the proximal length portion 38, which will be disposed within the proximal length portion 22 of the outer member 12 when the inner member is assembled with the outer member to cut anatomical tissue. The length segment 52 of the tubular body 43 may thusly be considered a distal length portion and will be disposed within the distal length portion 32 of the outer member 12 when the inner and outer members are assembled to cut anatomical tissue.

Figure 2:
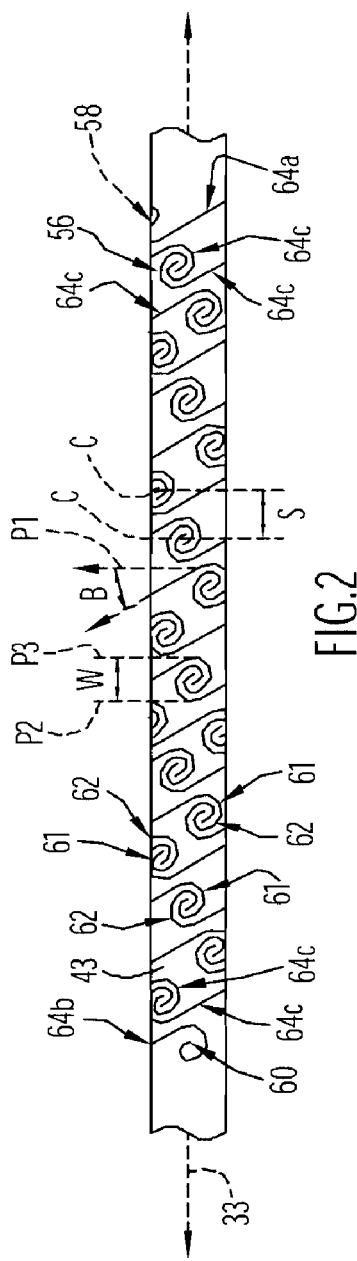
FIG. 2 is a broken side view of a flexible region of a flexible inner member of the angled rotary tissue cutting instrument.
Figure 4:
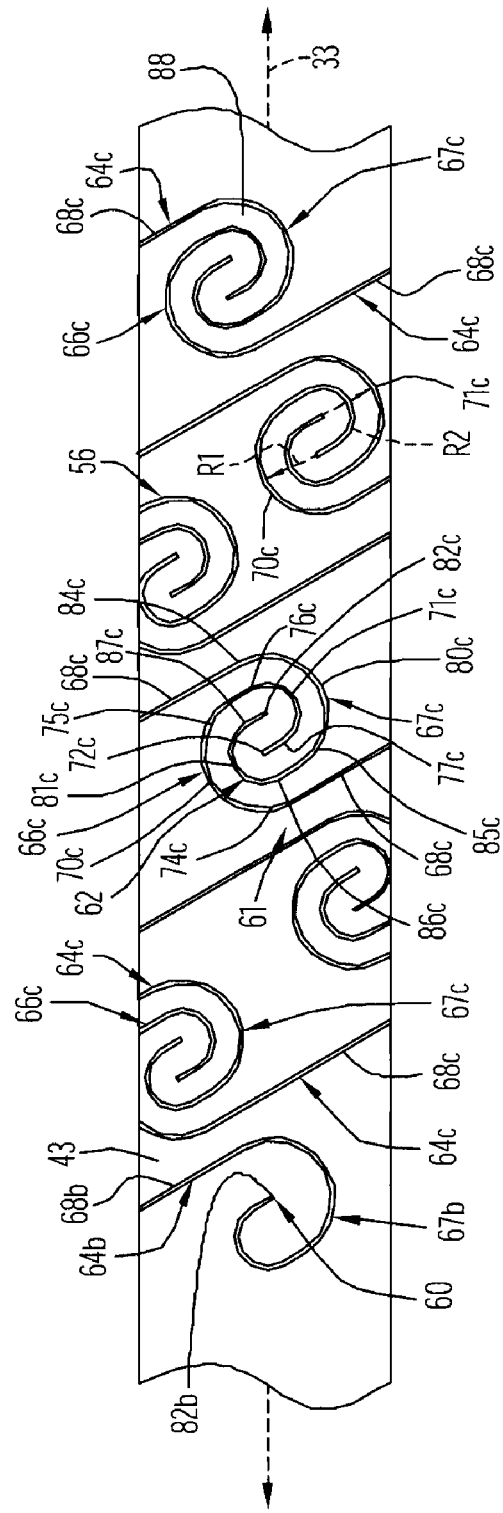
FIG. 4 is a broken, enlarged side view of the labyrinthine cut in the tubular body.
Figure 3:
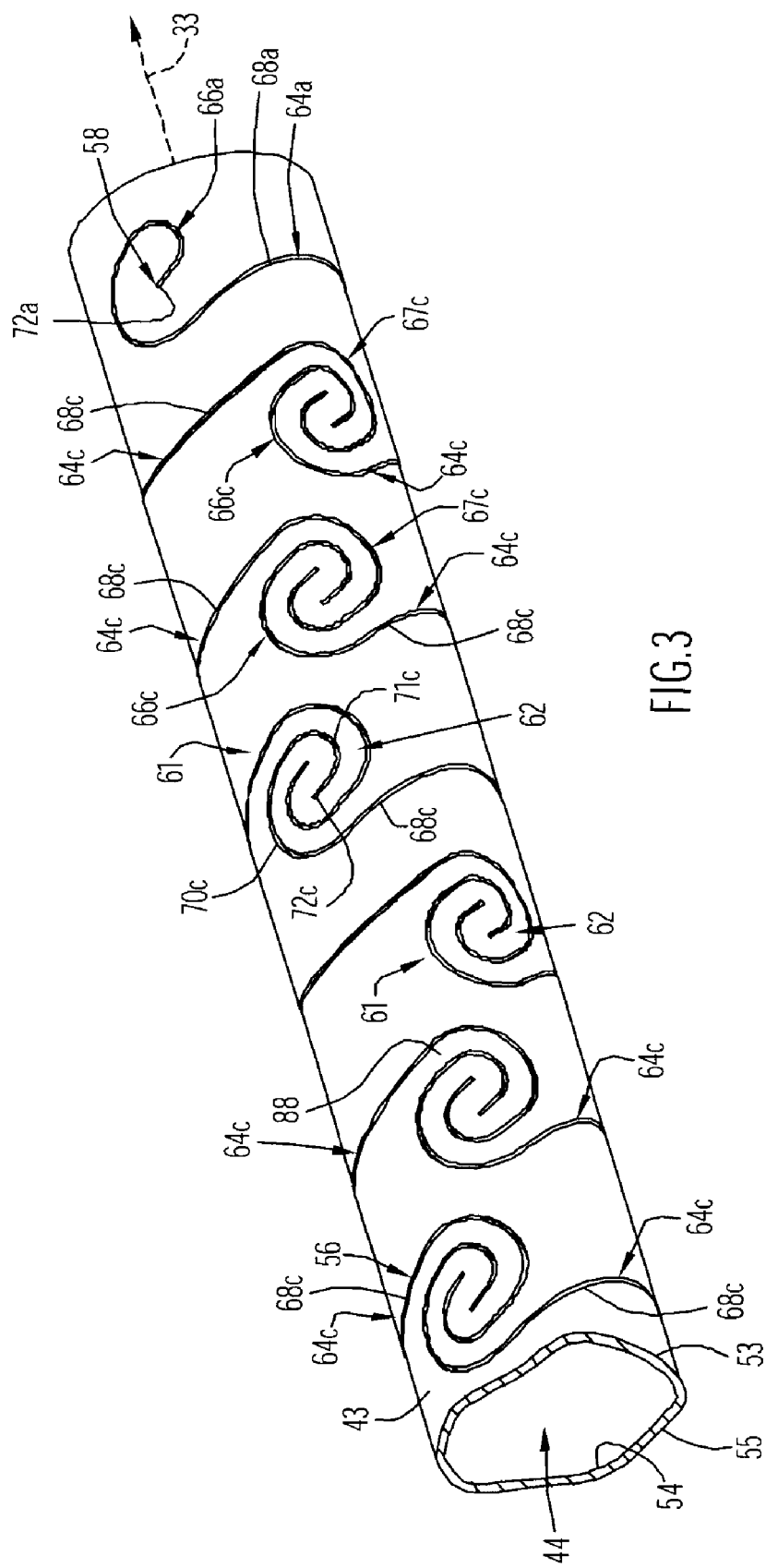
FIG. 3 is a broken perspective view of a tubular body having a labyrinthine cut therein comprising the flexible region of FIG. 2.

The flexible region 42, which is best depicted in FIGS. 2-4, comprises a labyrinthine cut 56 formed in the tubular body 43 of the inner member 14. As best shown in FIG. 3, the tubular body 43 has a cylindrical wall with an external diameter surface 53, an internal diameter surface 54 defining the lumen 44, and a radial wall thickness 55 between the external and internal diameter surfaces. Prior to the labyrinthine cut 56 being formed therein, the wall of the tubular body 43 along the flexible region 42 and along the length segments 50 and 52 is a rigid, integral and unitary, one piece or monolithic, solid, annular wall coaxial with the central longitudinal axis 33. The labyrinthine cut 56 extends through the entire wall thickness 55 of the cylindrical wall of the tubular body 43. The labyrinthine cut 56 has a starting end 58 on the tubular body 43 as seen in FIGS. 2 and 3, and has a terminating end 60 on the tubular body 43 as seen in FIGS. 2 and 4. The cut 56 extends rotationally about the central longitudinal axis 33 of the tubular body 43 in a forward direction or path from the starting end 58 to the terminating end 60. Looking from the starting end 58 toward the terminating end 60, the rotational direction for cut 56 is in a counterclockwise direction about the axis 33 from the starting end 58 to the terminating end 60. However, it should be appreciated that the cut could rotate about the axis 33 in a clockwise rotational direction looking from the starting end 58 toward the terminating end 60. Also, the cut 56 extends longitudinally along the tubular body 43 in the forward direction or path from the starting end 58 to the terminating end 60 of the cut. The labyrinthine cut 56 has a plurality of labyrinthine areas 61 between the starting end 58 and the terminating end 60 within which the cut 56 forms a labyrinth configuration 62 as explained further below. In the case of labyrinthine cut 56, the terminating end 60 is located on the tubular body 43 distally of the starting end 58, such that the forward direction or path of the cut 56 is in the distal direction along the inner member 14. It should be appreciated, however, that the starting and terminating ends can be reversed, such that the end 60 can be the starting end for the cut 56 and the end 58 can be the terminating end for the cut 56, in which case the forward direction or path of the cut is in the proximal direction along the inner member.

The labyrinthine cut 56 comprises a plurality of cut sections in the tubular body 43 having curled segments and being arranged in succession from the starting end 58 to the terminating end 60, such that each labyrinth configuration 62 is defined by the curled segment of a cut section in cooperative arrangement with an opposed curled segment of a next succeeding cut section in the forward direction or path of the cut 56. The labyrinthine cut 56 is discontinuous or interrupted between its starting end 58 and its terminating end 60, there being a break, gap, stop or interruption in the cut 56 within each labyrinth configuration 62. Accordingly, the plurality of cut sections that make up cut 56 are separate, disconnected cut sections in the tubular body 43, with each cut section having opposed end points on the tubular body 43 which are separated from the end points of the next succeeding and/or the next preceding cut section by uncut wall segments of the tubular body 43.

The cut sections for the labyrinthine cut 56 comprise a starting cut section 64a at the starting end 58, a terminating cut section 64b at the terminating end 60, and a plurality of intermediate cut sections 64c between the starting and terminating cut sections 64a and 64b. Each cut section 64c follows and is cut in the same pattern and includes opposed first and second curled segments 66c and 67c, each following a variably curving or multiply curving path, and a connecting segment 68c extending angularly from one curled segment to the other as best seen in FIGS. 3 and 4. The connecting segment 68c of the cut section extends rotationally about the central longitudinal axis 33 of the tubular body 43 from the first curled segment 66c to the second or succeeding curled segment 67c at a non-perpendicular angle to the central longitudinal axis 33 as explained further below. As best depicted in FIGS. 3 and 4, the curled segment 66c follows a variably or multiply curving path having a major curve 70c extending laterally away from the connecting segment 68c and having a minor curve 71c extending from the major curve 70c laterally back toward the connecting segment 68c to terminate at an end point 72c of the cut section 64c. The curled segment 66c thusly forms a first end segment of the cut section 64c. The major curve 70c is generally C-shaped in configuration with a mid-section or base between a pair of spaced apart arms. As best seen in FIGS. 3 and 4, the major curve 70c includes an inner arm 74c joined to, merging or continuous with the connecting segment 68c and an outer arm 75c joined to, merging or continuous with the minor curve 71c. The major curve 70c has a span or width between the inner and outer arms 74c and 75c. The minor curve 71c is generally C-shaped in configuration with a mid-section or base between a pair of spaced apart arms, but with a more pronounced curvature than and curving in the opposite or reverse direction from the C-shaped configuration of the major curve 70c. The minor curve 71c has an outer arm 76c joined to, merging or continuous with the outer arm 75c of the major curve 70c and has an inner arm 77c terminating at the end point 72c. The major curve 70c has a radius of curvature R1, and the minor curve 71c has a radius of curvature R2 smaller than the radius of curvature R1 as depicted in FIG. 4. The minor curve 71c has a span or width between the outer and inner arms 76c and 77c that is less than the span of the major curve 70c. The end point 72c is spaced from the mid-section of the major curve 70c in a direction radial to the major curve 70c. The end point 72c and the inner arm 77c of the minor curve 71c are situated mid-way between the confluence of outer arm 75c/outer arm 76c and the confluence of inner arm 74c/connecting segment 68c. The variably or multiply curving path followed by the curled segment 66c from the connecting segment 68c to the end point 72c is a continuously curving path in which the curled segment 66c curves or extends in a lateral direction away from the connecting segment 68c with a relatively gentle concave curve (major curve 70c) to an offset position spaced laterally from the connecting segment 68c, and then curves or extends with a reverse, relatively sharp or more pronounced concave curve and in the opposite direction laterally (minor curve 71c) toward the connecting segment 68c to a second offset position mid-way between the first offset position and the connecting segment 68c. The cut section 64c is an example of one in which the lateral direction that the major curve 70c curves or extends away from the connecting segment 68c is toward the proximal end or direction of the inner member 14.

The opposed curled segment 67c of the cut section 64c follows the same variably or multiply curving path as the curled segment 66c but is an inverted mirror image of the curled segment 66c. The major curve 80c of curled segment 67c curves or extends laterally away from the connecting segment 68c in the opposite lateral direction from the major curve 70c and is curved in a direction reverse from the direction of curvature of major curve 70c. In the case of cut section 64c, the major curve 80c curves or extends away from the connecting segment 68c in a lateral direction that is toward the distal end or direction of the inner member 14. The lateral direction in which the minor curve 81c of curled segment 67c extends from the major curve 80c back toward the connecting segment 68c is the reverse or opposite the lateral direction that the minor curve 71c of curled segment 66c extends from the major curve 70c back toward the connecting segment 68c. The major curve 80c has an inner arm 84c, an outer arm 85c and a span between the inner and outer arms 84c and 85c as described for major curve 70c. The minor curve 81c has an outer arm 86c, an inner arm 87c terminating at the opposite end point 82c, and a span between the outer and inner arms 86c and 87c as described for minor curve 71c. The curled segment 67c forms a second or succeeding end segment of the cut section 64c opposite the end segment formed by curled segment 66c. The major curve 80c has the radius of curvature R1, and the minor curve 81c has the radius of curvature R2. In the labyrinth configuration 62, the radius of curvature R2 is or is about one-half the radius of curvature R1.

The connecting segment 68c extends between the curled segments 66c and 67c at an acute angle B to a plane P1 perpendicular to the central longitudinal axis 33 of the tubular body 43 as seen in FIG. 2. In the case of labyrinthine cut 56, the connecting segments 68c extend angularly from the curled segments 66c to the curled segments 67c with a slant or angle toward the proximal end or direction of the inner member 14. The connecting segment 68c of each cut section may follow a linear course or path that is disposed in a plane that defines angle B with plane P1. The connecting segments 68c extend rotationally about the axis 33 in the rotational direction of the cut 56, i.e. counterclockwise in the case of cut 56. The connecting segments 68c of the cut sections 64c are of the same length between the curled segments 66c and 67c of the cut section. The cut sections 64c are of the same overall length between their end points 72c and 82c. The curled segments 66c and 67c of each cut section 64c are offset rotationally from one another on the tubular body 43. Furthermore, the curled segment 66c of each cut section 64c is located on the tubular body 43 proximally of its curled segment 67c. Accordingly, the curled segments 66c and 67c of each cut section 64c are offset longitudinally from one another on the tubular body 43.

The starting cut section 64a is like the cut sections 64c except that the starting cut section 64a may be provided with or without the first curled segment 66a shown in FIG. 3. The starting cut section 64a comprises a second or succeeding curled or end segment (not shown in the drawings) like the curled segments 67c and a connecting segment 68a like the connecting segments 68c of cut sections 64c. The cut section 64a is illustrated as having a first curled or end segment 66a configured like the curled segments 66c of cut sections 64c, and the end point 72a of the curled segment 66a is the starting end 58 of the cut 56 as seen in FIG. 3. However, the cut section 64a could be formed without the curled segment 66a, and an end point of the connecting segment 68a can serve as the starting end 58 of the cut 56. The terminating cut section 64b is like the cut sections 64c except that the terminating cut section 64b may be provided with or without the second curled segment 67b shown in FIG. 4. The terminating cut section 64b comprises a first curled or end segment (not visible in the drawings) like the curled segments 66c and a connecting segment 68b like the connecting segments 68c of cut sections 64c. The cut section 64b is illustrated as having a second curled segment 67b configured like the curled segments 67c of cut sections 64c, and the end point 82b of the curled segment 67b is the terminating end 60 of the cut 56 as seen in FIG. 4. However, the cut section 64b could be formed without the curled segment 67b, and an end point of the connecting segment 68b can serve as the terminating end 60 of the cut 56.

The cut sections 64a, 64b and 64c are formed in the tubular body 43 such that the second curled segments 67a, 67c are cooperatively arranged with the opposed first curled segments 66c, 66b of an adjacent or next succeeding cut section, i.e. the next cut section in or along the forward direction or path of the labyrinthine cut 56, to form labyrinthine areas 61 in which the cut defines the labyrinth configurations 62. Conversely, the opposed first curled segments 66c, 66b are cooperatively arranged with the second curled segments 67a, 67c of an adjacent or next preceding cut section, i.e. the next cut section in the reverse direction or path of the cut 56, to form the labyrinthine areas 61 containing the labyrinth configurations 62. The first labyrinthine area 61 in or along the forward direction or path of the cut 56 is the one formed by the cooperative arrangement of the second curled segment of the starting cut section 64a and the first curled segment 66c of the first intermediate cut section 64c, i.e. the intermediate cut section 64c that directly follows or next succeeds the starting cut section 64a in or along the forward direction or path of the cut 56. The last labyrinthine area 61 in or along the forward direction or path of the cut 56 is formed by the cooperative arrangement of the second curled segment 67c of the last intermediate cut section 64c and the first curled segment of the terminating cut section 64b, the last intermediate cut section being the intermediate cut section 64c that directly precedes or comes before the terminating cut section 64b. The labyrinthine areas 61 situated between the first and last labyrinthine areas are each formed by the cooperative arrangement of a second curled segment 67c of a cut section 64c with the first curled segment 66c of the next succeeding cut section. The connecting segment 68a extends in or along the forward direction or path away from the starting end 58 to the first labyrinthine area 61. The connecting segment 68b extends in or along the forward direction or path from the last labyrinthine area 61 toward the terminating end 60. Each connecting segment 68c extends in or along the forward direction or path from one labyrinthine area 61 to a next succeeding labyrinthine area 61. The connecting segments 68a, 68b and 68c are in alternating arrangement with the labyrinthine areas 61 in or along the forward direction or path of the cut 56, and the connecting segments 68a, 68b and 68c are parallel to one another along the tubular body 43.

An intermediate labyrinthine area 61 containing a labyrinth configuration 62 formed by the cooperative arrangement of a second curled segment 67c of an intermediate cut section 64c and a first curled segment 66c of a next succeeding intermediate cut section 64c is described with reference to FIG. 4. The first and last labyrinthine areas 61 are like the intermediate labyrinthine areas and contain labyrinth configurations 62 like the intermediate labyrinth configuration described with reference to FIG. 4. The minor curve 71c of curled segment 66c is arranged within or inside of the major curve 80c of curled segment 67c with the concave curves 71c and 80c being in spaced relation, the span of the minor curve 71c fitting within the span of the major curve 80c. The curves 71c and 80c are uniformly or substantially uniformly spaced from one another, and the curves 71c and 80c are thusly parallel or substantially parallel to one another. The minor curve 81c of curled segment 67c is arranged within or inside of the major curve 70c of curled segment 66c with the concave curves 81c and 70c being in spaced relation, the span of the minor curve 81c fitting within the span of the major curve 70c. The arrangement and spaced relationship between curves 81c and 70c is the same as that for curves 71c and 80c, except that the curves 81c,70c are of opposite curvature to the curves 71c,80c. The end point 72c of curled segment 66c is spaced away from the mid-section of minor curve 81c in a direction radial to the minor curve 81c and, conversely, the end point 82c of curled segment 67c is similarly but oppositely spaced away from the mid-section of minor curve 71c in a direction radial to the minor curve 71c. The mid-section of minor curve 81c is spaced away from the mid-section of major curve 70c in a direction radial to the major curve 70c. Conversely, the mid-section of minor curve 71c is similarly but oppositely spaced away from the mid-section of major curve 80c in a direction radial to the major curve 80c. The mid-section of minor curve 81c is disposed mid-way or substantially mid-way between the end point 72c and the mid-section of major curve 70c. Conversely, the mid-section of minor curve 71c is disposed mid-way or substantially mid-way between the end point 82c and the mid-section of major curve 80c. The inner arm 77c of the minor curve 71c of curled segment 66c is disposed mid-way or substantially mid-way between the arms 86c and 87c of the minor curve 81c of the curled segment 67c. Conversely, the inner arm 87c of the minor curve 81c of curled segment 67c is disposed mid-way or substantially mid-way between the arms 76c and 77c of the minor curve 71c of curled segment 66c. The major curves 70c and 80c are laterally offset relative to one another, and the minor curves 71c and 81c are laterally offset relative to one another while being disposed respectively within the major curves 80c, 70c. The end points 72c and 82c are laterally spaced or offset from one another and do not meet or connect due to the stop, interruption, gap or break in the cut 56 that occurs in the labyrinth configuration 62. The break in the cut 56 results in a gap between the end points 72c and 82c which is occupied by a solid uncut portion of the wall of the tubular body 43. As seen in FIG. 2, the labyrinth configurations 62 have a center C located along the gap mid-way between the end points 72c and 82c. As further seen in FIG. 2, the labyrinth configurations 62 have a width W between a plane P2 perpendicular to the central longitudinal axis 33 and tangential to the major curve 70c, and a plane P3 parallel to plane P2 and tangential to the major curve 80c, the width W being parallel to axis 33. The curled segments 66c and 67c are uniformly or substantially uniformly spaced from one another in the labyrinth configuration 62. Each labyrinth configuration 62 can be considered as comprising two major concave curves, i.e. a first major curve 70c and a second major curve 80c, that curve in opposite directions to one another, and two minor concave curves, i.e. a first minor curve 71c and a second minor curve 81c, that curve in opposite directions to one another. The wall of the tubular body 43 in the labyrinthine area 61 is formed into a narrow, sinuous track 88 of material of uniform or substantially uniform width that, in the forward direction or path of the cut 56, follows the labyrinth configuration 62 by taking a first large bend of relatively gentle curvature between the major curve 80c and the minor curve 71c, followed by a first smaller bend of relatively sharper curvature between minor curve 81c and end point 72c in the reverse direction from the first large bend, followed by a second smaller bend of the relatively sharper curvature between minor curve 71c and end point 82c in the reverse direction from the first smaller bend, followed by a second large bend of the relatively gentle curvature between the major curve 70c and the minor curve 81c in the reverse direction from the second smaller bend. The track 88 formed in the wall of the tubular body 43 thusly comprises two gently curved or bent large bends of opposite curvature or bend joined by two relatively more sharply curved or bent smaller bends of opposite curvature or bend. Also, the sinuous track 88 is a continuous segment of the tubular body wall through the labyrinthine area 61. The labyrinthine area 61 is situated between the connecting segments 68c of the cut sections 64c whose curled segments 66c and 67c form the labyrinthine area, the connecting segments 68c being longitudinally offset from each other along the tubular body 43. In particular, the connecting segment 68c of the succeeding cut section 64c is longitudinally offset distally or forwardly from the connecting segment 68c of the preceding cut section 64c. There is a center-to-center longitudinal spacing S between the labyrinth configurations 62 in successive cycles, revolutions or turns of the cut 56 in the forward direction or path about the central longitudinal axis 33 of the tubular body 43 as seen in FIG. 2. The labyrinthine cut 56 can be formed in the tubular body 43 in any suitable manner, preferably by laser cutting the tubular body 43. The radial dimension or thickness of the annular wall of the inner tubular member 14 along the flexible region 42 is the same as the wall thickness 55 of the tubular body 43 along the labyrinthine cut region of the body 43, which is the same as the wall thickness along the solid, rigid, uncut segments 50, 52 of the cylindrical wall of the body 43.

In one illustrative preferred embodiment, the radius of curvature R1 is or is about 0.025 inch; the radius of curvature R2 is or is about 0.0125 inch; the width W is or is about 0.08 inch; the spacing S is or is about 0.10 inch; the angle B is or is about 20°; the labyrinthine areas repeat at or about three labyrinthine areas per revolution or turn of the cut 56 about the axis 33; the terminating end of the cut 56 is or is about 0.50 inch from the distal tip of the cutting element; and the length of the labyrinthine cut region of the tubular body from the starting end to the terminating end of the cut is or is about 2.0 inches.

The flexible region 42 has numerous advantages including, but not limited to, appropriate rigidity and torsional strength, the ability to transmit torque at bend angles of up to 90°, greater resistance to stretching in the longitudinal direction of the inner tubular member 14, and preservation of the integrity of the internal diameter of the tubular body 43 when transmitting torque during rotation of the inner tubular member 14 within the angled outer tubular member 12. The flexible region 42 has the further advantage of not requiring any additional structural component(s) and/or material(s) over or within the labyrinthine cut in order to operate effectively as the flexible region for an inner member of an angled rotary tissue cutting instrument. An additional advantage is that the annular wall thickness of the inner member 14 along the flexible region 42 can be better minimized in order to better minimize the external diameter of the inner member and/or to better maximize the internal diameter of the inner member. Also, eliminating the need for additional structural components and/or materials presents the advantage of allowing the flexible region 42 to be produced at lower cost and with greater structural simplicity for a reduced risk of operational problems. Although the flexible region 42 does not require any additional structural component(s) over the labyrinthine cut, it is possible to provide a very thin-walled sleeve or sheath over the labyrinthine cut region of the tubular body while retaining the aforementioned advantages. The flexible region 42 is especially well-suited for use with an angled outer tubular member 12 having a bend angle A of up to 90°.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An angled rotary tissue cutting instrument for cutting anatomical tissue, comprising
   an elongate angled outer tubular member having a distal end, a longitudinal internal passage, an open proximal end communicating with said passage, an angled region between said distal end and said proximal end, and an opening in said distal end communicating with said passage; and
   a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotated within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external diameter surface, an internal diameter surface, and a wall thickness between said external diameter surface and said internal diameter surface, said flexible region consisting of a labyrinthine cut formed in said tubular body to extend entirely through said wall thickness, said tubular body being a rigid tube prior to said labyrinthine cut being formed therein, said labyrinthine cut having a starting end on said tubular body and a terminating end on said tubular body, said labyrinthine cut extending longitudinally along said tubular body and extending rotationally about said central longitudinal axis in a forward direction of said labyrinthine cut from said starting end to said terminating end, said labyrinthine cut including a plurality of labyrinthine areas rotationally spaced about said central longitudinal axis, said labyrinthine cut defining a labyrinth configuration in each of said labyrinthine areas, said labyrinthine cut consisting of a plurality of disconnected cut sections arranged in succession on said tubular body in said forward direction of said labyrinthine cut, each of said cut sections having a single connecting segment connected with no more than two curled segments respectively disposed at opposite ends of said connecting segment and curling in opposite directions from said connecting segment, each of said labyrinthine areas being formed by the cooperative arrangement of one curled segment of a cut section with an opposed curled segment of a next succeeding cut section in said forward direction, each of said labyrinth configurations comprising a first major curve and a first minor curve defined by said one curled segment and a second major curve and a second minor curve defined by said opposed curled segment, said first minor curve being joined to said first major curve and being of reverse curvature to said first major curve, said second minor curve being of reverse curvature to said first minor curve, said second major curve being joined to said second minor curve and being of reverse curvature to said second minor curve, said first minor curve being disposed within said second major curve and being spaced from said second major curve in a direction radial to said second major curve, said second minor curve being disposed within said first major curve and being spaced from said first major curve in a direction radial to said first major curve, said labyrinthine cut in said tubular body imparting sufficient strength and rigidity to said flexible region for said flexible region to transmit torque to rotate said cutting element to cut anatomical tissue.

2. The angled rotary tissue cutting instrument recited in claim 1 wherein said major curves have a radius of curvature, and said minor curves have a radius of curvature smaller than said radius of curvature of said major curves.

3. The angled rotary tissue cutting instrument recited in claim 1 wherein said connecting segments alternate with said labyrinthine areas in said forward direction of said labyrinthine cut, each of said labyrinth configurations has said first major curve joined to one of said connecting segments and has said second major curve joined to a next succeeding one of said connecting segments in said forward direction of said labyrinthine cut.

4. The angled rotary tissue cutting instrument recited in claim 3 wherein said next succeeding one of said connecting segments extends in said forward direction of said labyrinthine cut from said second major curve of said labyrinth configuration to a first major curve of a next succeeding one of said labyrinth configurations.

5. The angled rotary tissue cutting instrument recited in claim 4 wherein said connecting segments extend in said forward direction of said labyrinthine cut in the same rotational direction about said central longitudinal axis and at a non-perpendicular angle to said central longitudinal axis.

6. The angled rotary tissue cutting instrument recited in claim 5 wherein each of said connecting segments is disposed at an acute angle to a plane perpendicular to said central longitudinal axis.

7. The angled rotary tissue cutting instrument recited in claim 5 wherein said connecting segments are parallel to one another along said tubular body.

8. The angled rotary tissue cutting instrument recited in claim 1 wherein said first minor curve terminates at a first end point in each of said labyrinth configurations, said second minor curve terminates at a second end point within each of said labyrinth configurations, said first end point is spaced from said second end point by a gap in said labyrinthine cut in each of said labyrinth configurations, each of said cut sections being spaced from a next succeeding one of said cut sections by one of said gaps.

9. An angled rotary tissue cutting instrument for cutting anatomical tissue, comprising
an elongate angled outer tubular member having a distal end, a longitudinal internal passage, an open proximal end communicating with said passage, an angled region between said distal end and said proximal end, and an opening in said distal end communicating with said passage; and
a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotated within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external diameter surface, an internal diameter surface, and a wall thickness between said external diameter surface and said internal diameter surface, said flexible region consisting of a labyrinthine cut formed in said tubular body to extend entirely through said wall thickness, said tubular body being a rigid tube prior to said labyrinthine cut being formed therein, said labyrinthine cut having a single starting end on said tubular body and a single terminating end on said tubular body, said labyrinthine cut extending longitudinally along said tubular body and extending rotationally about said central longitudinal axis in a forward direction of said labyrinthine cut from said starting end to said terminating end, said labyrinthine cut including a plurality of labyrinthine areas rotationally spaced about said central longitudinal axis, said labyrinthine cut defining a labyrinth configuration in each of said labyrinthine areas, said labyrinthine cut consisting of a plurality of disconnected cut sections having the same pattern and arranged in succession on said tubular body in said forward direction of said labyrinthine cut, each of said cut sections having a single connecting segment connected with no more than two curled segments respectively disposed at opposite ends of said connecting segment and curling in opposite directions from said connecting segment, each of said labyrinthine areas being formed by the cooperative arrangement of one curled segment of a cut section with an opposed curled segment of a next succeeding cut section in said forward direction, each of said labyrinth configurations comprising a first major curve and a first minor curve defined by said one curled segment and a second major curve and a second minor curve defined by said opposed curled segment, said first major curve having a mid-section between inner and outer arms, a said first minor curve being of reverse curvature to said first major curve and having an inner arm, an outer arm continuous with said outer arm of said first major curve, and a mid-section between said inner and outer arms of said first minor curve, said second minor curve curving in the same direction as said first major curve and being disposed within said first major curve in spaced relation to said first major curve, said second minor curve having an inner arm, an outer arm, and a mid-section between said inner and outer arms of said second minor curve, said second major curve curving in the same direction as said first minor curve and having an inner arm, an outer arm continuous with said outer arm of said second minor curve, and a mid-section between said inner and outer arms of said second major curve, said first minor curve being disposed within said second major curve in spaced relation to said second major curve, said labyrinthine cut in said tubular body imparting sufficient strength and rigidity to said flexible region for said flexible region to transmit torque to rotate said cutting element to cut anatomical tissue.

10. The angled rotary tissue cutting instrument recited in claim 9 wherein said first minor curve is spaced from said second major curve in a direction radial to said second major curve, and said second minor curve is spaced from said first major curve in a direction radial to said first major curve.

11. The angled rotary tissue cutting instrument recited in claim 10 wherein said inner arm of said first minor curve is disposed between said outer arm of said second minor curve and said inner arm of said second minor curve, said inner arm of said second minor curve is disposed between said outer arm of said first minor curve and said inner arm of said first minor curve.

12. The angled rotary tissue cutting instrument recited in claim 11 wherein each of said inner arms has an end point in said labyrinth configuration and a gap in said labyrinthine cut between said end points.

13. The angled rotary tissue cutting instrument recited in claim 9 wherein said first minor curve is in parallel spaced relation to said second major curve, and said second minor curve is in parallel spaced relation to said first major curve.

14. The angled rotary tissue cutting instrument recited in claim 9 wherein said first and second major curves have a radius of curvature, and said first and second minor curves have a radius of curvature one-half said radius of curvature of said first and second major curves.

15. The angled rotary tissue cutting instrument recited in claim 14 wherein said radius of curvature of said first and second major curves is 0.025 inch and said radius of curvature of said first and second minor curves is 0.0125 inch.

16. An angled rotary tissue cutting instrument for cutting anatomical tissue, comprising
an elongate angled outer tubular member having a distal end, a longitudinal internal passage, an open proximal end communicating with said passage, an angled region between said distal end and said proximal end, and an opening in said distal end communicating with said passage; and
a flexible inner member for being rotatably disposed within said outer tubular member, said inner member having a distal end, a proximal end, a tubular body between said distal end of said inner member and said proximal end of said inner member, a cutting element at said distal end of said inner member, said cutting element being exposed from said opening to cut anatomical tissue when said inner member is rotated within said outer tubular member, and a flexible region for being disposed within said angled region to transmit torque to rotate said cutting element while conforming to the configuration of said angled region when said inner member is rotated within said outer tubular member, said tubular body having a central longitudinal axis and a cylindrical wall with an external diameter surface, an internal diameter surface, and a wall thickness between said external diameter surface and said internal diameter surface, said flexible region comprising a labyrinthine cut formed in said tubular body to extend entirely through said wall thickness, said tubular body being a rigid tube prior to said labyrinthine cut being formed therein, said labyrinthine cut having a starting end on said tubular body and a terminating end on said tubular body, said labyrinthine cut extending longitudinally along said tubular body and extending rotationally about said central longitudinal axis in a forward direction of said labyrinthine cut from said starting end to said terminating end, said labyrinthine cut including a plurality of labyrinthine areas rotationally spaced about said central longitudinal axis, said labyrinthine cut defining a labyrinth configuration in each of said labyrinthine areas, said labyrinthine cut consisting of a plurality of identical disconnected cut sections arranged in succession in said forward direction of said labyrinthine cut, said plurality of cut sections including a plurality of intermediate cut sections in succession between said starting end and said terminating end, each of said intermediate cut sections consisting of a first curled segment, a second curled segment, and a connecting segment extending in said forward direction of said labyrinthine cut from said first curled segment to said second curled segment, said first curled segment and said second curled segment curving from said connecting segment in opposite directions, each of said intermediate cut sections having said second curled segment arranged with said first curled segment of a next succeeding one of said cut sections to define one of said labyrinth configurations, said connecting segments extending in the same rotational direction about said central longitudinal axis and at the same non-perpendicular angle to said central longitudinal axis, said labyrinthine cut in said tubular body imparting sufficient strength and rigidity to said flexible region for said flexible region to transmit torque to rotate said cutting element to cut anatomical tissue.

17. The angled rotary tissue cutting instrument recited in claim 16 wherein said plurality of cut sections further includes a starting cut section beginning at said starting end and including a second curled segment and a connecting segment extending away from said starting end in said forward direction of said labyrinthine cut to said second curled segment of said starting cut section, and a terminating cut section ending at said terminating end and including a first curled segment and a connecting segment extending from said first curled segment of said terminating cut section in said forward direction of said labyrinthine cut toward said terminating end, said second curled segment of said starting cut section being arranged with said first curled segment of the next succeeding one of said intermediate cut sections to define one of said labyrinth configurations, said first curled segment of said terminating cut section being arranged with said second curled segment of the next preceding one of said intermediate cut sections to define one of said labyrinth configurations.

18. The angled rotary tissue cutting instrument recited in claim 17 wherein said first curled segments define a major concave curve extending in a lateral direction away from one end of a corresponding one of said connecting segments with a first radius of curvature and a minor concave curve extending from said major concave curve in the opposite lateral direction toward said corresponding one of said connecting segments with a second radius of curvature, smaller than said first radius of curvature, in an opposite direction of curvature from said major concave curve, said second curled segments define a major reverse concave curve extending in said opposite lateral direction away from an opposite end of said corresponding one of said connecting segments with said first radius of curvature in a direction of curvature the same as said minor concave curve, and a minor reverse concave curve extending from said major reverse concave curve in said lateral direction toward said corresponding one of said connecting segments with said second radius of curvature in the same direction of curvature as said major concave curve.

19. The angled rotary tissue cutting instrument recited in claim 17 wherein said cut sections are separated from one another by gaps in said labyrinthine cut respectively located between end points of said first and second curled segments within each of said labyrinth configurations.

20. The angled rotary tissue cutting instrument recited in claim 17 wherein said starting cut section includes a first curled segment having an end point forming said starting end, and said terminating cut section includes a second curled segment having an end point forming said terminating end.

* * * * *